ically, US010421676B2

(12) United States Patent
Yoneda et al.

(10) Patent No.: US 10,421,676 B2
(45) Date of Patent: Sep. 24, 2019

(54) BACTERICIDAL/ALGICIDAL METHOD

(75) Inventors: Yutaka Yoneda, Tokyo (JP); Hideo Otaka, Tokyo (JP); Kouichi Tanaka, Tokyo (JP); Kazuhiko Tsunoda, Tokyo (JP); Naohiro Nagai, Tokyo (JP); Akira Iimura, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 142 days.

(21) Appl. No.: 12/733,746

(22) PCT Filed: Sep. 10, 2008

(86) PCT No.: PCT/JP2008/066338
§ 371 (c)(1),
(2), (4) Date: May 14, 2010

(87) PCT Pub. No.: WO2009/041267
PCT Pub. Date: Apr. 2, 2009

(65) Prior Publication Data
US 2010/0240535 A1     Sep. 23, 2010

(30) Foreign Application Priority Data

Sep. 27, 2007 (JP) ............................ 2007-252303
Feb. 21, 2008 (JP) ............................ 2008-039924

(51) Int. Cl.
| C02F 1/76 | (2006.01) |
| A01N 59/00 | (2006.01) |
| A01N 25/22 | (2006.01) |
| A01N 59/02 | (2006.01) |

(52) U.S. Cl.
CPC ............... *C02F 1/76* (2013.01); *A01N 59/00* (2013.01); *A01N 59/02* (2013.01); *C02F 2209/04* (2013.01); *Y02W 10/37* (2015.05)

(58) Field of Classification Search
CPC ........ C02F 1/76; C02F 2209/04; A01N 59/00; A01N 59/02; Y02W 10/37
USPC ............................................................ 504/151
See application file for complete search history.

(56) References Cited

U.S. PATENT DOCUMENTS

| 3,170,883 | A | 2/1965 | Owen et al. |
| 5,683,654 | A | 11/1997 | Dallmier et al. |
| 5,948,315 | A | 9/1999 | Yang et al. |
| 6,110,387 | A | 8/2000 | Choudhury et al. |
| 6,471,974 | B1 | 10/2002 | Rees et al. |
| 6,669,904 | B1 | 12/2003 | Yang et al. |
| 2002/0056689 | A1 | 5/2002 | Shim et al. |
| 2007/0265181 | A1* | 11/2007 | Kikuchi et al. ............... 510/125 |

FOREIGN PATENT DOCUMENTS

| EP | 1 287 741 A1 | 3/2003 |
| JP | 2003-146817 | 5/2003 |
| JP | 2003215119 A * | 7/2003 |
| JP | 2003-267812 | 9/2003 |
| JP | 2006-206608 | 8/2006 |
| WO | WO 97/34827 | 9/1997 |
| WO | WO 01/42145 | 6/2001 |
| WO | WO 2007/050162 | 5/2007 |

OTHER PUBLICATIONS

Morita, S. (JP 2003267812A), Sep. 2003, Derwent Abstract, pp. 1-4.*
Morita et al. JP 2003-267812, 2003, Internet Translation, pp. 1-5.*
Chlorine Residual (DL2). Publication, Lab Manual [online]. VT Water Quality, 1998, [retrieved on May 18, 2014]. Retrieved from the Internet<http://www.vtwaterquality.org/ww/om/LabManual/ChlorineResidual.pdf> 24 pages.*
Suehiro (JP 2003-215119A), Internet Translation, PAJ, 4 pages.*
CL17 Chlorine Analyzer, Instrument Manual (Cat. No. 24400-18), 2002, Hach Company, pp. 1-68.*

* cited by examiner

*Primary Examiner* — John Pak
*Assistant Examiner* — Andriae M Holt
(74) *Attorney, Agent, or Firm* — Manabu Kanesaka

(57) ABSTRACT

The invention provides a bactericidal/algicidal method including adding an oxidant-based bactericidal/algicidal agent and a stabilizer therefor to a target water system, characterized in that the amount of combined chlorine or the stabilizer in the water system is controlled by generating free residual chlorine in the water system, and a bactericidal/algicidal method including adding an oxidant-based bactericidal/algicidal agent and a stabilizer therefor to a target water system, characterized in that the amount of the oxidant-based bactericidal/algicidal agent added is controlled so that the concentration of total residual chlorine in the water system falls within a predetermined range, and the amount of combined chlorine or the stabilizer is controlled so that the concentration of free residual chlorine in the water system falls within a predetermined range.

An object of the present invention is to provide a bactericidal/algicidal method including adding an oxidant-based bactericidal/algicidal agent and a stabilizer therefor to a target water system for bactericidal/algicidal treatment, wherein the amount of combined chlorine or the stabilizer is controlled, and the amount of the oxidant-based bactericidal/algicidal agent added is controlled, which method realizes effective utilization of the stabilizer, to thereby reduce the amount of the stabilizer employed and to reduce COD and the amount of nitrogen derived from the stabilizer, and which method does not require a special control apparatus for in-line mixing as described above.

5 Claims, 4 Drawing Sheets

BACTERICIDAL/ALGICIDAL METHOD

RELATED APPLICATIONS

The present application is National Phase of International Application No. PCT/JP2008/066338 filed Sep. 10, 2008, and claims priority from Japanese Application No. 2007-252303, filed Sep. 27, 2007 and No. 2008-039924, filed Feb. 21, 2008, the disclosure of which is hereby incorporated by reference herein in its entirety.

TECHNICAL FIELD

The present invention relates to a method for killing bacteria and/or algae (hereinafter may be referred to as a "bactericidal/algicidal method"), in which an oxidant-based bactericidal/algicidal agent and a stabilizer therefor are added to a water system (e.g., a cooling water system, a paper mill water system, a dust collecting water system, a scrubber water system, a wastewater treatment system, a water system for cutting oil, and a fountain water system), whereby bactericidal/algicidal treatment is carried out.

BACKGROUND ART

In a variety of water systems, bacteria or algae cause various problems. For example, in open-circulating cooling water systems, bacteria (e.g., zoogleal bacteria, filamentous bacteria, iron bacteria, sulfur bacteria, nitrifying bacteria, and sulfate-reducing bacteria), fungi (e.g., saprolegnia and penicillium), or algae (e.g., blue-green algae, green algae, and diatom) are grown, and slime or sludge is generated through deposition or accumulation of ooze-like contaminants formed through mixing of such microorganisms (main components) with, for example, inorganic substances (e.g., earth and sand) or dust. The thus-generated slime or sludge reduces thermal efficiency and water circulation, and causes local corrosion in apparatuses or piping. In some cases, bacteria grown in a water system cause damage directly to a human body, e.g., legionnaires' disease induced by Legionella dispersed from a cooling tower.

Also, in a paper mill water system, slime is generated through growth of, for example, various bacteria, fungi, or yeast, and the thus-generated slime causes defects (e.g., holes, spots, or blots) in a product, to thereby lower the quality thereof, or causes breakage of a paper sheet, to thereby reduce productivity.

Hitherto, such bacteria- or algae-caused problems in a water system have been prevented by adding a chlorine-containing oxidant like a hypochlorite salt to the water system. In general, when the residual chlorine concentration of water is 5 mg-$Cl_2$/L or higher, growth of bacteria or algae in the water can be prevented. Since decomposition of such a chlorine-containing oxidant is promoted by UV rays, when a bactericidal/algicidal agent containing such a chlorine-containing oxidant as an active ingredient is charged into, for example, a plastic container and is stored or allowed to stand outside, the chlorine-containing oxidant is decomposed by UV rays. In the case of, for example, an open-circulating cooling water system to which such a bactericidal/algicidal agent has been added, difficulty is encountered in completely shielding the cooling water from light. Since piping or a heat exchanger of such a water system is made of, for example, copper or a copper alloy, decomposition of such a chlorine-containing oxidant is further promoted through elution of copper ions.

There is disclosed a technique for reducing decomposition of such a chlorine-containing oxidant; i.e., a method including adding, to a water system, a composition containing a hypochlorite salt, benzotriazole or tolyltriazole, and a sulfamate salt serving as a chlorine stabilizer, in which the effective chlorine component of the oxidant is stabilized by adjusting the pH of the composition to 13 or higher (see Patent Document 1).

When a sulfamate salt is added to a hypochlorite salt, a stabilized hypochlorite salt (combined chlorine), e.g., an N-monochlorosulfamate salt or an N,N-dichlorosulfamate salt is formed; i.e., the effective chlorine component of the hypochlorite salt is stabilized.

However, such a stabilized hypochlorite salt is considerably decomposed in a target water system containing a large amount of slime, or under strong UV irradiation or high-temperature conditions. Therefore, problems arise in that the concentration of the stabilized hypochlorite salt is difficult to maintain constant even under control of the amount of combined chlorine added by means of, for example, a batch timer or makeup water proportional control, and in that a large amount of a sulfamate salt as a stabilizer must be used.

In the case of, for example, a water system in which combined chlorine is consumed in a large amount, the amount of combined chlorine detected in the water system tends to be smaller than the amount of combined chlorine that has actually been added. When the amount of combined chlorine added is increased so as to maintain the effective chlorine detection level, running cost increases, and combined chlorine consumed in the water system remains therein a stabilizer in a large amount.

That is, when such a stabilized hypochlorite salt is decomposed in a water system, the resultant hypochlorite salt is consumed in the water system, but the resultant sulfamate salt remains therein. When the remaining sulfamate salt is discharged outside the water system, the sulfamate salt affects nitrogen regulation and COD regulation.

There is also proposed a composition containing a stabilized hypochlorite salt and a triazole compound (e.g., benzotriazole) (see Patent Document 2). However, when such a composition is used in a water system, the aforementioned sulfamate salt and a triazole compound (e.g., benzotriazole) are discharged outside the water system through blowing down, and the discharged salt and compound further affect nitrogen regulation and COD regulation.

Hitherto, a stabilized hypochlorite salt solution added to a water system has generally been prepared through in-line mixing of a hypochlorite salt solution and a sulfamate salt solution so that the hypochlorite salt and the sulfamate salt are present in equimole amounts.

This preparation requires a special control apparatus for in-line mixing of the two components so that they are present in equimole amounts.

Patent Document 1: Japanese Patent No. 3832399
Patent Document 2: Japanese Patent Application Laid-Open (kokai) No. 2006-206608

DISCLOSURE OF THE INVENTION

Problems to be Solved by the Invention

In view of the foregoing, an object of the present invention is to provide a bactericidal/algicidal method including adding an oxidant-based bactericidal/algicidal agent and a stabilizer therefor to a target water system for bactericidal/algicidal treatment, wherein the amount of combined chlorine or the stabilizer is controlled, and the amount of the oxidant-based bactericidal/algicidal agent added is controlled, which method realizes effective utilization of the stabilizer, to thereby reduce the amount of the stabilizer employed and to reduce COD and the amount of nitrogen derived from the stabilizer, and which method does not require a special control apparatus for in-line mixing as described above.

Means for Solving the Problems

In order to achieve the aforementioned object, the present inventors have conducted extensive studies, and as a result have found that the object can be attained by controlling the amount of combined chlorine or a stabilizer so that the concentration of free residual chlorine in a water system falls within a predetermined range. The present invention has been accomplished on the basis of this finding.

Accordingly, the present invention provides the following.

1. A bactericidal/algicidal method comprising adding an oxidant-based bactericidal/algicidal agent and a stabilizer therefor to a target water system, characterized in that the amount of combined chlorine or the stabilizer in the water system is controlled by generating free residual chlorine in the water system.
2. A bactericidal/algicidal method as described in 1 above, wherein the amount of combined chlorine or the stabilizer is controlled by controlling the concentration of free residual chlorine in the water system.
3. A bactericidal/algicidal method as described in 1 or 2 above, wherein the concentration of free residual chlorine in the water system is 0.05 mg-Cl/L or higher.
4. A bactericidal/algicidal method as described in any of 1 to 3 above, wherein the oxidant-based bactericidal/algicidal agent is at least one species selected from the group consisting of hypochlorous acid, chlorous acid, chlorine dioxide, hypobromous acid, salts of these acids, and chlorine gas.
5. A bactericidal/algicidal method as described in any of 1 to 4 above, wherein the stabilizer is sulfamic acid and/or a salt thereof.
6. A bactericidal/algicidal method comprising adding an oxidant-based bactericidal/algicidal agent and a stabilizer therefor to a target water system, characterized in that the amount of the oxidant-based bactericidal/algicidal agent added is controlled so that the concentration of total residual chlorine in the water system falls within a predetermined range, and the amount of combined chlorine or the stabilizer is controlled so that the concentration of free residual chlorine in the water system falls within a predetermined range.
7. A bactericidal/algicidal method as described in 6 above, wherein the oxidant-based bactericidal/algicidal agent is at least one species selected from the group consisting of hypochlorous acid, chlorous acid, chlorine dioxide, hypobromous acid, salts of these acids, and chlorine gas.
8. A bactericidal/algicidal method as described in 6 or 7 above, wherein the amount of the oxidant-based bactericidal/algicidal agent added is controlled so that the concentration of total residual chlorine in the water system falls within a range of 0.1 to 100 mg-Cl/L, and the amount of the stabilizer added is controlled so that the concentration of free residual chlorine in the water system falls within a range of 1 mg-Cl/L or less.
9. A bactericidal/algicidal method as described in any of 6 to 8 above, wherein the stabilizer is sulfamic acid and/or a salt thereof.

Effects of the Invention

According to the present invention, there is provided a bactericidal/algicidal method including adding an oxidant-based bactericidal/algicidal agent and a stabilizer therefor to a target water system for bactericidal/algicidal treatment, wherein the amount of combined chlorine or the stabilizer is controlled, and the amount of the oxidant-based bactericidal/algicidal agent added is controlled. The bactericidal/algicidal method realizes effective utilization of the stabilizer, to thereby reduce the amount of the stabilizer employed and to reduce COD and the amount of nitrogen derived from the stabilizer, and the method does not require a special control apparatus for in-line mixing as described above.

DESCRIPTION OF REFERENCE NUMERALS

1. Cooling tower
2. Cooling water pipe
3. Heat exchanger
5. Free chlorine control section

BEST MODES FOR CARRYING OUT THE INVENTION

The present invention will next be described in detail. Specific embodiments described hereinbelow are given only for the illustration purpose and should not be construed as limiting the invention thereto.

In the bactericidal/algicidal method of the present invention, free chlorine is generated in a water system, to thereby control the amount of combined chlorine or a chlorine stabilizer in the water system. Free chlorine generated in the water system can bind to the chlorine stabilizer remaining in the water system. Thus, combined chlorine can be regenerated. In the present invention, when free chlorine is generated in water to be treated, combined chlorine can be effectively regenerated by, at least, causing free chlorine to remain in the water system at a predetermined concentration or higher.

In the bactericidal/algicidal method of the present invention, in which an oxidant-based bactericidal/algicidal agent and a stabilizer therefor are added to a target water system, the amount of the oxidant-based bactericidal/algicidal agent added is controlled so that the concentration of total residual chlorine in the water system falls within a predetermined range, and the amount of the stabilizer added is controlled so that the concentration of free residual chlorine in the water system falls within a predetermined range.

The oxidant-based bactericidal/algicidal agent employed in the method of the present invention may be a compound which has conventionally been known as an oxidant-based bactericidal/algicidal agent. Examples of the compound include hypochlorous acid and salts thereof, chlorous acid and salts thereof, chloric acid and salts thereof, perchloric acid and salts thereof, chlorinated isocyanuric acid and salts thereof, chlorine gas, and chlorine dioxide. Specific examples of acid salts include alkali metal hypochlorites such as sodium hypochlorite and potassium hypochlorite; alkaline earth metal hypochlorites such as calcium hypochlorite and barium hypochlorite; alkali metal chlorites such as sodium chlorite and potassium chlorite; alkaline earth metal chlorites such as calcium chlorite and barium chlorite; other metal chlorites such as nickel chlorite; ammonium chlorate; alkali metal chlorates such as sodium chlorate and potassium chlorate; and alkaline earth metal chlorates such as calcium chlorate and barium chlorate. Hypobromite salts may be employed in place of hypochlorite salts.

These oxidants may be employed singly or in combination of two or more species. Among these oxidants, hypochlorite salts are preferably employed, from the viewpoint of easy handling.

When a hypobromite salt is employed in place of or in addition to a hypochlorite salt, the concentration of the hypobromite salt is represented as reduced to chlorine.

Hypobromite salt concentration is converted based on the following relation: hypochlorous acid (52.5 g/L)=hypobromous acid (97.5 g/L)=chlorine (71 g/L).

Decomposition of such a hypochlorite salt or hypobromite salt is promoted by UV rays. Therefore, in the present invention, the aforementioned oxidant-based bactericidal/algicidal agent and a stabilizer therefor are added to a target water system, so as to reduce decomposition of the agent(s) and to stabilize the effective chlorine component of the agent.

The stabilizer for the aforementioned oxidant-based bactericidal/algicidal agent employed in the method of the present invention may be appropriately selected from among compounds which have conventionally been known as stabilizers for the oxidant-based bactericidal/algicidal agent. Specific examples of such a stabilizer include sulfamic acid and/or salts thereof, azole compounds, urea, thiourea, creatinine, cyanuric acid, alkyl hydantoin, monoethanolamine, diethanolamine, organic sulfonamide, biuret, organic sulfamic acid, and melamine. Of these, preferred are sulfamic acid and/or salts thereof, which are effectively employed as stabilizers for a hypochlorite salt or a hypobromite salt. Examples of the sulfamic acid salt which may be employed include, but are not particularly limited to, sodium sulfamate, potassium sulfamate, calcium sulfamate, strontium sulfamate, barium sulfamate, iron sulfamate, and zinc sulfamate. Of these, sodium sulfamate is preferred, from the viewpoints of water solubility and cost.

In the present invention, sulfamic acid and salts thereof may be employed singly or in combination of two or more species.

For example, a hypochlorite ion reacts with sulfamic acid as shown in the following reaction scheme, whereby an N-monochlorosulfamate ion or an N,N-dichlorosulfamate ion is formed, and the effective chlorine component of the chlorine-containing oxidant is stabilized, to thereby generate combined chlorine.

Examples of the combined chlorine species generated in a manner similar to that described above include chloramine-T (Sodium N-chloro-4-methylbenzenesulfonamide), chloramine-B (Sodium N-chloro-benzenesulfonamide), Sodium N-chloro-p-nitrobenzenesulfonamide, trichloromelamine, mono- or di-chloromelamine sodium or potassium salt, trichloroisocyanurate, mono- or di-chloroisocyanurate sodium or potassium salt, monochlorohydantoin, 1,3-dichlorohydantoin, and a 5,5-alkyl derivative thereof.

A mono- or di-chlorosulfamate ion exhibits a bactericidal effect lower than that of a free chlorine ion.

Meanwhile, a hypobromite ion reacts with sulfamic acid as shown in the following reaction scheme, whereby an N-monobromosulfamate ion or an N,N-dibromosulfamate ion is formed, and the effective bromine component of the bromine-containing oxidant is stabilized.

A mono- or di-bromosulfamate ion exhibits a bactericidal effect almost comparable to that of a free bromine ion.

In the bactericidal/algicidal method of the present invention, the amount of combined chlorine or a chlorine stabilizer in a water system is controlled by generating free chlorine in the water system. When free chlorine is generated in the water system, as described above, the free chlorine can bind to the chlorine stabilizer remaining in the water system, to thereby regenerate combined chlorine. Thus, when a chlorine-containing oxidant is caused to coexist, in water to be treated, with, for example, a sulfamic acid compound or a chlorosulfamate-containing combined chlorine formed from the chlorine-containing oxidant and the sulfamic acid compound, the free chlorine concentration of the water does not considerably vary in a wide pH range (from acidic to alkaline).

No particular limitation is imposed on the method for generating free chlorine in a water system, so long as the method can generate free chlorine in a water system. Examples of the method include, but are not limited to, a method in which the aforementioned chlorine-containing or bromine-containing agent is added to a water system, and a method in which a hypochlorite ion is generated through electrolysis of, for example, brine or an aqueous potassium chloride solution.

Generation of free chlorine may be carried out in consideration of the concentration of a chlorine stabilizer remaining in a water system. The remaining chlorine stabilizer binds to free chlorine to form combined chlorine, and excess free chlorine can be detected as is. Combined chlorine can be effectively regenerated by controlling the concentration of free chlorine so as to fall within a predetermined range.

Preferably, the amount of combined chlorine is controlled on the basis of the concentration of free chlorine in the water system. When a chlorine-containing oxidant is added from outside to the water system in which the stabilizer remains, to thereby generate free chlorine, and the concentration of the thus-generated free chlorine is continuously monitored, excess free chlorine can be detected in a real-time manner. Thus, the amount of combined chlorine or the stabilizer in the water system can be controlled in a real-time manner, and excessive addition of combined chlorine or the stabilizer can be effectively prevented.

If necessary, the method of the present invention may also employ control means for measuring the concentration of free chlorine in a water system, and controlling the amount of free chlorine in the water system on the basis of the thus-measured free chlorine concentration. The quality of water in the water system can be continuously controlled through this control means. No particular limitation is imposed on the control means, and the amount of free chlorine may be controlled by, for example, adding a chlorine-containing agent on the basis of the measured chlorine concentration.

No particular limitation is imposed on the method for measuring the concentration of free chlorine in a water system. Examples of the measuring method include a method in which chlorine concentration is measured through polarography, absorption spectroscopy, or the DPD (N,N-diethylphenylenediamine) method, and a method in which oxidation-reduction potential (ORP) is measured in a water system, and free chlorine concentration is estimated on the basis of the thus-measured ORP.

In the bactericidal/algicidal method of the present invention, the amount of any of the aforementioned oxidant-based bactericidal/algicidal agents added is controlled so that the concentration of total residual chlorine in a target water system falls within a predetermined range, and the amount of any of the combined chlorine species or stabilizers is controlled so that the concentration of free residual chlorine in the water system falls within a predetermined range.

Specifically, bactericidal/algicidal treatment is carried out by controlling the amount of the oxidant-based bactericidal/algicidal agent added so that the concentration of total residual chlorine in the target water system (as measured by means of a chlorine-concentration-measuring apparatus) preferably falls within a range of 0.1 to 100 mg-Cl/L, more preferably 1 to 100 mg-Cl/L, and by controlling the amount of combined chlorine or stabilizer so that the concentration of free residual chlorine in the water system preferably falls within a range of 1 mg-Cl/L or less, more preferably 0.5 mg-Cl/L or less, much more preferably 0.3 mg-Cl/L or less.

Preferably, the amount of the stabilizer added is controlled so that the amount by mole of the stabilizer is generally 0.5 to 2.0 times that of the oxidant-based bactericidal/algicidal agent added.

The concentration of combined chlorine in the water system preferably falls within a range of 0.1 mg-Cl/L (lower limit) to 50 mg-Cl/L (upper limit).

Advantageously, such bactericidal/algicidal treatment is carried out by controlling the pH of the water system so as to fall within a range of 3.0 to 10.0 (preferably 6.0 to 9.0).

Specific methods for measuring the aforementioned total residual chlorine concentration and free residual chlorine concentration will be described in detail hereinbelow.

Bactericidal/algicidal activity is preferably enhanced by increasing total residual chlorine concentration. In such a case, stabilizer becomes deficient by increasing free residual chlorine concentration, whereas free residual chlorine concentration is reduced by increasing stabilizer concentration. Such a concentration control may be automatically or manually carried out.

The amount of an oxidant-based bactericidal/algicidal agent added may be controlled by means of an on-line total residual chlorine concentration analyzer, while the amount of a stabilizer added is controlled by means of an on-line free residual chlorine concentration analyzer.

No particular limitation is imposed on the water system to which the bactericidal/algicidal method of the present invention is applied, and the water system may be, for example, a cooling water system, a paper mill water system, a dust collecting water system, a scrubber water system, a wastewater treatment system, a water system for cutting oil, or a fountain water system.

In the case where the bactericidal/algicidal method of the present invention is applied to such a target water system, even when the water system is irradiated with sunlight, or the water system employs, for example, piping or a heat exchanger made of copper or a copper alloy, the concentration of residual chlorine concentration in the water system is maintained at high level, and thus bactericidal/algicidal treatment can be effectively carried out in the water system. In addition, since a stabilizer is effectively utilized in the water system, the amount of the stabilizer employed can be reduced, and thus COD and the amount of nitrogen derived from the stabilizer can be reduced.

EXAMPLES

The present invention will next be described in more detail by way of examples, which should not be construed as limiting the invention thereto.

In Examples 1 to 3 described hereinbelow, free residual chlorine concentration and total residual chlorine concentration were measured through the following methods.
(1) Free Residual Chlorine Concentration
(a) Preparation of DPD Reagent N,N-Diethyl-phenylenediamine sulfate (1.0 g) is mixed with anhydrous sodium sulfate (24 g), to thereby prepare a DPD (N,N-diethyl-p-phenylenediamine) reagent.
(b) Preparation of Phosphate Buffer (pH=6.5)

0.2 mol/L Sodium hydroxide solution (35.4 mL) is added to 0.2 mol/L potassium dihydrogenphosphate (100 mL), and trans-1,2-cyclohexanediaminetetraacetic acid monohydrate (0.13 g) is dissolved in the resultant mixture, to thereby prepare a phosphate buffer (pH=6.5).
(c) Measurement of Free Residual Chlorine Concentration The phosphate buffer (2.5 mL) is placed in a container (50 mL) having a stopper, and the DPD reagent (0.5 g) is added thereto. Subsequently, test water is added to the container so that the total amount of the mixture is 50 mL, followed by mixing. Thereafter, an appropriate amount of the resultant solution is placed in an absorption cell, and absorbance is measured at about 510 to about 555 nm by means of a photoelectric spectrophotometer. Free residual chlorine concentration is determined on the basis of a calibration curve which has been prepared in advance.
(2) Total Residual Chlorine Concentration Potassium iodide (about 0.5 g) is added to and dissolved in the solution obtained above in (1) (c) (50 mL), and the resultant solution is allowed to stand still for about three minutes. Thereafter, in a manner similar to that described above in (1) (c), absorbance is measured at about 510 to about 555 nm by means of a photoelectric spectrophotometer, and total residual chlorine concentration is determined on the basis of a calibration curve which has been prepared in advance.

Example 1

Stabilization of Hypochlorite Salt

Sodium hypochlorite (0.014 mmol/L) (total residual chlorine concentration: 1 mg-Cl/L) was added to simulated cooling water (M-alkalinity: 250 mg-Cl/L, calcium hardness: 250 mg-Cl/L, and magnesium hardness: 125 mg-Cl/L) (1 L) at 30° C. Sodium sulfamate was added to the cooling water so that the amount by mole of sodium sulfamate was 1, 2, or 5 times that of the effective chlorine component of sodium hypochlorite.

As a result, free residual chlorine concentration was found to be maintained at a low level about 24 hours after initiation of reaction of the hypochlorite salt with the sulfamate salt (the ratio by mole of the sulfamate salt to the effective chlorine component of the hypochlorite salt=1 or more).

Figure 1:
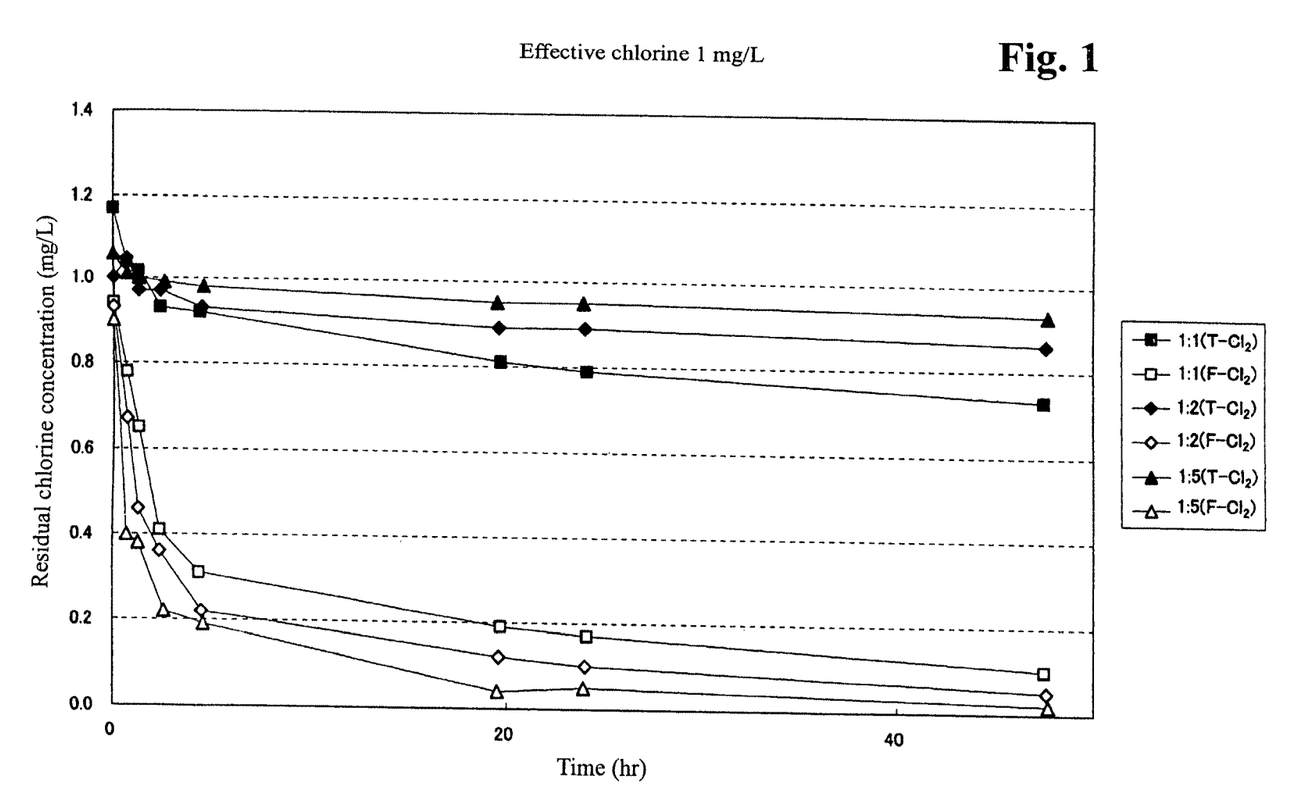
FIG. 1 is a graph showing changes over time of residual chlorine concentrations in Example 1.

The results are shown in Table 1 and FIG. 1. In Tables 1 and 2 and FIGS. 1 to 3, "T-$Cl_2$" represents total residual chlorine concentration; "F—$Cl_2$" represents free residual chlorine concentration; and "NT" represents stabilized hypochlorite salt concentration ([T-$Cl_2$]—[F—$Cl_2$]).

TABLE 1

| Time (hr) | T-$Cl_2$ (mg/L) | F-$Cl_2$ (mg/L) | NT (mg/L) | pH |
|---|---|---|---|---|
| Total residual chlorine = 1 mg/L, Ratio by mole of sulfamate/chlorine = 1 | | | | |
| 0 | 1.17 | 0.94 | 0.23 | 8.76 |
| 0.7 | 1.04 | 0.78 | 0.26 | 8.78 |
| 1.3 | 1.02 | 0.65 | 0.37 | 8.77 |
| 2.4 | 0.93 | 0.41 | 0.52 | 8.81 |
| 4.4 | 0.92 | 0.31 | 0.61 | 8.79 |
| 19.7 | 0.81 | 0.19 | 0.62 | 9.05 |
| 24.1 | 0.79 | 0.17 | 0.62 | 8.80 |
| 47.5 | 0.73 | 0.10 | 0.63 | 8.82 |
| Total residual chlorine = 1 mg/L, Ratio by mole of sulfamate/chlorine = 2 | | | | |
| 0 | 1.00 | 0.93 | 0.07 | 8.76 |
| 0.7 | 1.05 | 0.67 | 0.38 | 8.81 |
| 1.3 | 0.97 | 0.46 | 0.51 | 8.83 |
| 2.4 | 0.97 | 0.36 | 0.61 | 8.82 |
| 4.5 | 0.93 | 0.22 | 0.71 | 8.88 |
| 19.6 | 0.89 | 0.12 | 0.77 | 8.96 |
| 24.0 | 0.89 | 0.10 | 0.79 | 8.81 |
| 47.6 | 0.86 | 0.05 | 0.81 | 8.85 |
| Total residual chlorine = 1 mg/L, Ratio by mole of sulfamate/chlorine = 5 | | | | |
| 0 | 1.06 | 0.90 | 0.16 | 8.77 |
| 0.7 | 1.01 | 0.40 | 0.61 | 8.80 |
| 1.3 | 1.00 | 0.38 | 0.62 | 8.80 |
| 2.6 | 0.99 | 0.22 | 0.77 | 8.81 |
| 4.6 | 0.98 | 0.19 | 0.79 | 8.81 |
| 19.5 | 0.95 | 0.04 | 0.91 | 8.99 |
| 23.9 | 0.95 | 0.05 | 0.90 | 8.80 |
| 47.7 | 0.93 | 0.02 | 0.91 | 8.84 |

Example 2

Method for Regenerating Stabilized Hypochlorite Salt Consumed by Contaminants

Sodium hypochlorite (0.0705 mmol/L) (effective chlorine concentration: 5 mg-Cl/L) and sodium sulfamate (0.3525 mmol/L) (5 times (by mole) the amount of the effective chlorine component of sodium hypochlorite) were added to simulated cooling water (M-alkalinity: 250 mg-Cl/L, calcium hardness: 250 mg-Cl/L, and magnesium hardness: 125 mg-Cl/L) (1 L) at 30° C. Contaminants collected from an actual cooling water system were added to the cooling water so as to attain a turbidity of 100. The effective chlorine component was consumed by the contaminants. Total residual chlorine concentration was reduced from 5 mg-Cl/L (initial) to 1.5 mg-Cl/L in about three days. At this point in time, sodium hypochlorite was added (effective chlorine concentration: 5 mg-Cl/L), whereby total residual chlorine concentration increased to 6.5 mg-Cl/L. Virtually no free residual chlorine was detected; i.e., a stabilized hypochlorite salt was regenerated. Thereafter, the effective chlorine component was consumed again by the contaminants, and total residual chlorine concentration tended to be reduced.

Figure 2:
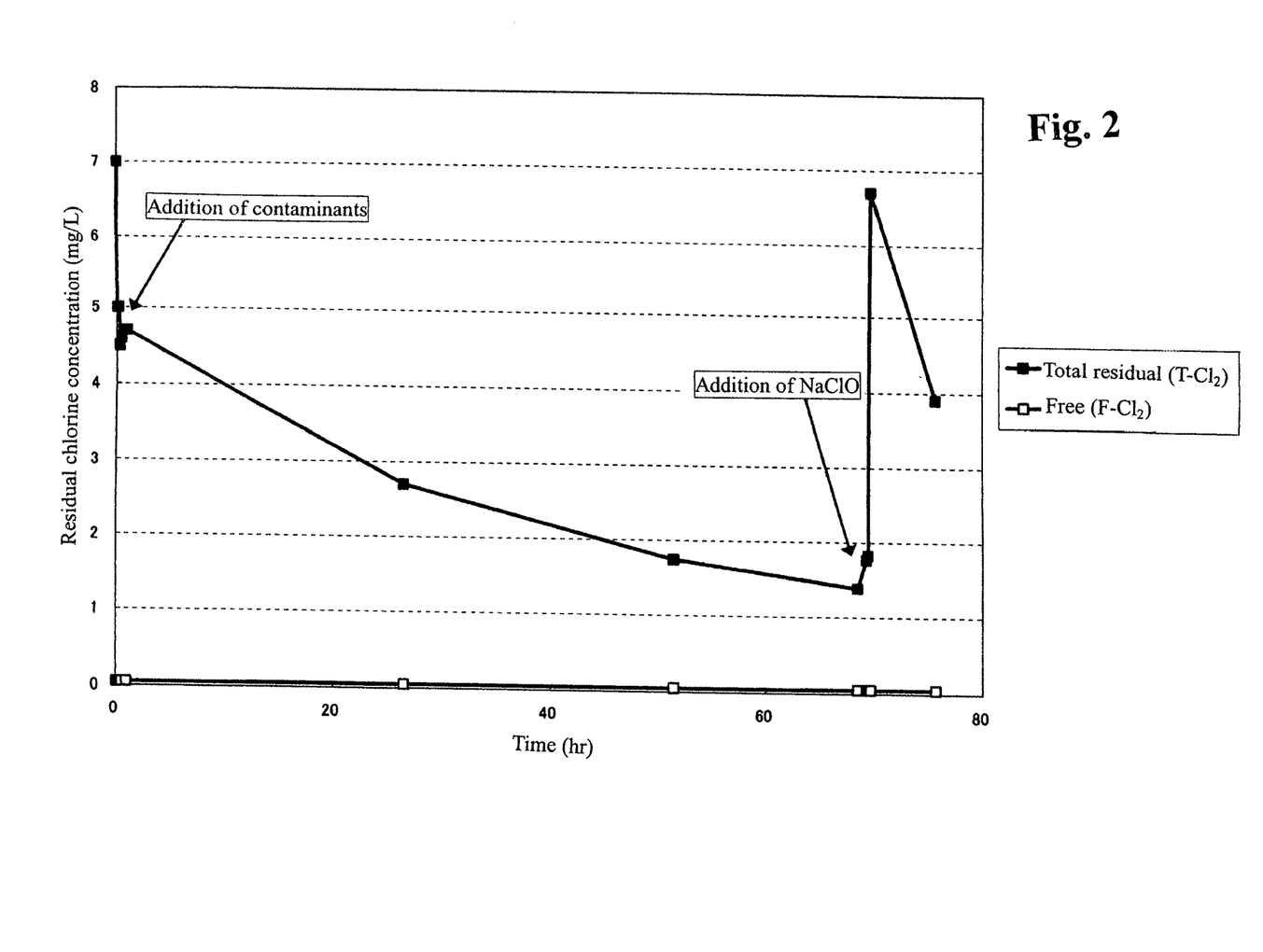
FIG. 2 is a graph showing changes over time of residual chlorine concentrations in Example 2.

The results are shown in FIG. 2.

The effective chlorine component (hypochlorite salt) is consumed by the contaminants, but the sulfamate salt remains in the water system. When the hypochlorite salt is further added to the water system, the hypochlorite salt reacts with the sulfamate salt remaining in the water system, to thereby regenerate a stabilized hypochlorite salt.

Thus, chlorine concentration can be controlled in an actual water system as follows. When the concentration of the effective chlorine component of a stabilized hypochlorite salt (total residual chlorine concentration) is reduced, the concentration of the effective chlorine component (total residual chlorine concentration) is maintained at a predetermined level through addition of a hypochlorite salt. When the hypochlorite salt is excessively added with respect to a sulfamate salt, free residual chlorine is detected. In this case, when the sulfamate salt is further added, free residual chlorine concentration can be reduced, and the stabilized hypochlorite salt can be regenerated.

Example 3

Reactivity Between Sulfamate Salt and Hypochlorite Salt

Sodium hypochlorite (0.084 mmol/L) (total residual chlorine concentration: 6 mg-Cl/L) was added to simulated cooling water (M-alkalinity: 250 mg-Cl/L, calcium hardness: 250 mg-Cl/L, and magnesium hardness: 125 mg-Cl/L) (1 L) at 30° C. Sodium sulfamate was added to the cooling water so that the amount by mole of sodium sulfamate was 0.83, 1.7, or 4.2 times that of the effective chlorine component of sodium hypochlorite, followed by examination of change over time in T-$Cl_2$ or F—$Cl_2$. The results are shown in Table 2 and FIG. 3.

Figure 3:
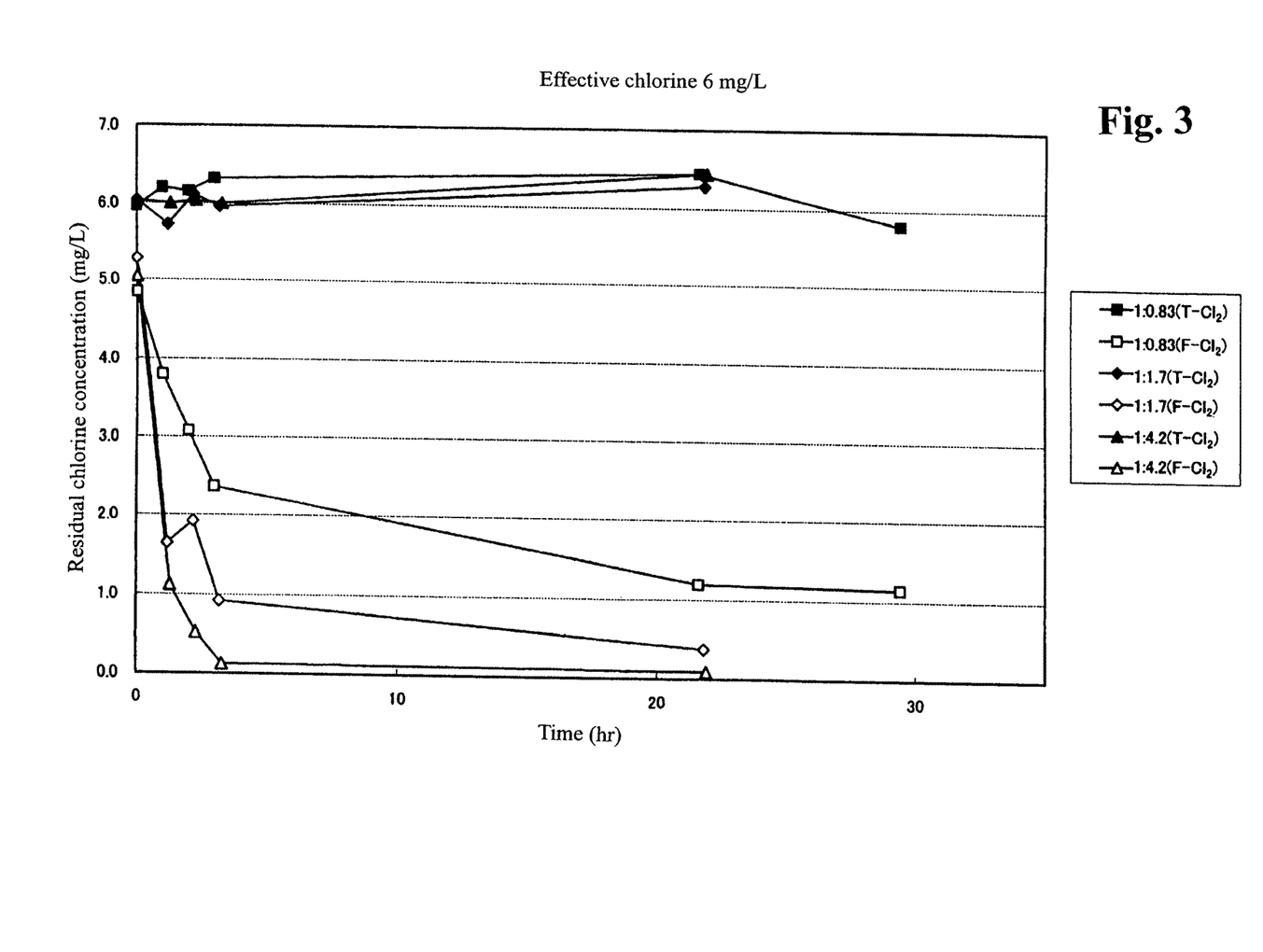
FIG. 3 is a graph showing changes over time of residual chlorine concentrations in Example 3.

As shown in Table 2 and FIG. 3, 22 hours after initiation of reaction of the hypochlorite salt with the sulfamate salt (the ratio by mole of the sulfamate salt to the effective chlorine component of the hypochlorite salt=1 or more), a stabilized hypochlorite salt was found to be generated, and free residual chlorine concentration was found to be maintained at a low level. Comparison between Table 1 and Table 2 shows that the rate of generation of the stabilized hypochlorite salt increases in accordance with an increase in total residual chlorine concentration from 1 mg-Cl/L to 6 mg-Cl/L.

TABLE 2

| Time (hr) | T-$Cl_2$ (mg/L) | F-$Cl_2$ (mg/L) | NT (mg/L) | pH |
|---|---|---|---|---|
| Total residual chlorine = 6 mg/L, Ratio by mole of sulfamate/chlorine = 0.83 | | | | |
| 0 | 5.96 | 4.84 | 1.12 | 8.92 |
| 1.0 | 6.20 | 3.80 | 2.40 | 8.83 |
| 2.0 | 6.16 | 3.08 | 3.08 | 8.83 |
| 3.0 | 6.32 | 2.36 | 3.96 | 8.81 |
| 21.6 | 6.44 | 1.19 | 5.25 | 8.85 |
| 29.4 | 5.80 | 1.14 | 4.66 | 8.84 |
| Total residual chlorine = 6 mg/L, Ratio by mole of sulfamate/chlorine = 1.7 | | | | |
| 0 | 6.04 | 5.28 | 0.76 | 8.95 |
| 1.2 | 5.72 | 1.64 | 4.08 | 8.88 |
| 2.2 | 6.12 | 1.92 | 4.20 | 8.82 |
| 3.2 | 5.96 | 0.92 | 5.04 | 8.68 |
| 21.8 | 6.28 | 0.37 | 5.91 | 8.87 |
| Total residual chlorine = 6 mg/L, Ratio by mole of sulfamate/chlorine = 4.2 | | | | |
| 0 | 6.04 | 5.04 | 1.00 | 8.88 |
| 1.3 | 6.00 | 1.12 | 4.88 | 8.83 |
| 2.3 | 6.04 | 0.52 | 5.52 | 8.89 |
| 3.3 | 6.00 | 0.12 | 5.88 | 8.88 |
| 21.9 | 6.44 | 0.09 | 6.35 | 8.86 |

Example 4

Figure 4:
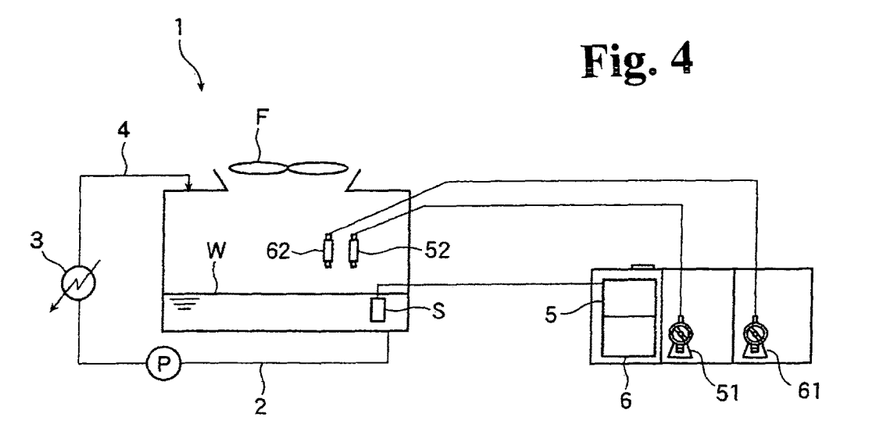
FIG. 4 shows an open-circulating cooling water system employed in Example 4.

The method of the present invention was verified by use of an apparatus shown in FIG. 4. FIG. 4 shows an open-circulating cooling water system employed in Example 4. In this open-circulating cooling water system, cooling water is supplied from a cooling tower 1 to a heat exchanger 3 via a cooling water pipe 2 and a pump P, and is returned to the cooling tower 1 via a cooling water pipe 4. The cooling tower 1 (refrigeration capacity: 400 RT, water storage capacity: 30 m$^3$) was operated at a concentration factor of 5. The cooling tower 1 has a fan F and contains therein air-conditioning cooling water W. The free chlorine concentration of the air-conditioning cooling water W is measured by means of a sensor S and controlled by means of a free chlorine control section 5 and a combined chlorine control section 6. The free chlorine control section 5 includes a chemical tank 51 and a chemical feed inlet 52. Combined chlorine control section 6 includes a chemical tank 61 and a chemical feed inlet 62. The amount of free chlorine or combined chlorine is controlled on the basis of the free chlorine concentration as measured by means of the sensor S employing an ORP electrode.

The amount of free chlorine was controlled through addition of a hypochlorite salt. Chlorosulfamic acid was employed as combined chlorine.

In the water system, chlorosulfamic acid was added so that the chlorine concentration was adjusted to 15 mg-Cl/L with respect to blowing down the cooling water. In the water system, the amount of the hypochlorite salt added was controlled by means of the sensor S so that free chlorine concentration was 0.5 mg-Cl/L. Combined chlorine concentration was measured through the DPD method (determined by use of the following relation: combined chlorine concentration=total residual chlorine concentration−free chlorine concentration).

Flaked slime was non-forcedly discharged through blowing down at an intensity according to the concentration factor, and a forced removal of the slime (e.g., cleaning) was not carried out. Thus, the water system was continuously operated, and change over time in combined chlorine concentration and free chlorine concentration in the water system was observed. The results are shown in Table 3.

Comparative Example 1

The water system was continuously operated under the same conditions as in Example 4 (i.e., chlorosulfamic acid was added so that the chlorine concentration was adjusted to 15 mg-Cl/L with respect to blowing down the cooling water), except that free chlorine concentration was not controlled. The results are shown in Table 3.

TABLE 3

| | Example 4 | | Comparative Example 1 | |
|---|---|---|---|---|
| Period (days) | Combined chlorine (mg/L) | Free chlorine (mg/L) | Combined chlorine (mg/L) | Free chlorine (mg/L) |
| 1 | 7 | 0.5 | 3 | 0.0 |
| 2 | 8 | 0.6 | 4 | 0.0 |
| 8 | 14 | 0.4 | 3 | 0.1 |
| 14 | 11 | 0.5 | 2 | 0.0 |
| 20 | 13 | 0.5 | 4 | 0.1 |

As shown in Table 3, in Example 4, combined chlorine concentration was maintained at high level, as compared with the case of Comparative Example 1. Particularly, in Example 4, combined chlorine concentration increased as the operation period of the water system was prolonged, and this change in combined chlorine concentration suggested that the combined chlorine was regenerated in the water system. These data indicate that, in Example 4, the concentration of the combined chlorine detected was maintained nearly equal to that of the combined chlorine compound added.

In contrast, in Comparative Example 1, combined chlorine concentration was maintained at low level throughout the operation period, which suggests that the combined chlorine was not regenerated due to no generation of free chlorine in the water system.

These data indicate that the method of the present invention realizes control of chlorine-combined compound concentration and regeneration of a consumed chlorine-combined compound, and a consistent bactericidal/algicidal effect is obtained through the method.

INDUSTRIAL APPLICABILITY

The bactericidal/algicidal method of the present invention is a technique in which an oxidant-based bactericidal/algicidal agent (e.g., a hypochlorite salt) is effectively reacted in just proportion with a sulfamate salt, to thereby generate a stabilized hypochlorite salt. The method of the present invention is widely applicable to a variety of water systems, including a cooling water system requiring bactericidal/algicidal treatment.

The invention claimed is:

1. A bactericidal/algicidal method, comprising:
    adding an oxidant-based bactericidal/algicidal agent and a stabilizer to a target water system thereby generating free residual chlorine in the water system; wherein the amount by mole of the stabilizer added is 0.5 to 5.0 times that of the oxidant-based bactericidal/algicidal agent;
    measuring a concentration of a total residual chlorine in the water system; and
    measuring a concentration of the free residual chlorine in the water system;
    wherein the measuring of the concentration of the free residual chlorine includes
        preparing a DPD (N,N-diethyl-p-phenylenediamine) reagent containing, N,N-diethyl-phenylenediamine sulfate and anhydrous sodium sulfate,
        mixing sodium hydroxide solution with potassium dihydrogenphosphate and trans-1,2-cyclohexanediaminetetraacetic acid monohydrate thereby preparing a phosphate buffer,
        mixing the DPD reagent, the phosphate buffer, and water sampled from the water system thereby preparing a resultant solution, and
        measuring an absorbance of the resultant solution at 510-555 nm with a photoelectric spectrophotometer, wherein the free residual chlorine concentration is determined on the basis of a calibration curve which has been prepared in advance, and
    wherein the measuring of the concentration of the total residual chlorine includes
        adding and dissolving potassium iodide to the resultant solution and allowing the resultant solution to which the potassium iodide is added to stand, and
        measuring an absorbance of the resultant solution to which the potassium iodide is added at 510-555 nm with the photoelectric spectrophotometer, wherein the total residual chlorine concentration is determined on the basis of a calibration curve which has been prepared in advance, and wherein the concentration of the total residual chlorine in the water system is maintained and controlled at 0.1 to 100 mg-Cl/L by adding an effective amount of the oxidant-based bactericidal/algicidal agent to the water system, wherein the concentration of the free residual chlorine in the water system is maintained and controlled at 0.05 to 1 mg-Cl/L by adding an effective amount of the stabilizer to the water system, and wherein the oxidant-based bactericidal/algicidal agent is hypochlorous acid or salt thereof, and the stabilizer is sulfamic acid or a salt thereof.

2. A bactericidal/algicidal method as described in claim 1, further comprising increasing a concentration of the stabilizer thereby reducing the concentration of the free residual chlorine in the water system when the concentration of the free residual chlorine in the water system is increased.

3. A bactericidal/algicidal method as described in claim 1, wherein the oxidant-based bactericidal/algicidal agent and the stabilizer are added separately.

4. A bactericidal/algicidal method as described in claim 1, further comprising controlling the amount of the stabilizer added by an on-line free residual chlorine concentration analyzer.

5. A bactericidal/algicidal method as described in claim 4, further comprising controlling the amount of the oxidant-based bactericidal/algicidal agent added by an on-line total residual chlorine concentration analyzer.

* * * * *